US008597941B2

(12) United States Patent
Shin et al.

(10) Patent No.: US 8,597,941 B2
(45) Date of Patent: Dec. 3, 2013

(54) BIOREACTOR FOR QUANTIFICATION OF HEADSPACE VOC CONTENT FROM CULTURES

(75) Inventors: Hye-Won Shin, Irvine, CA (US); Brandon J. Umber, Corona Del Mar, CA (US); Donald R. Blake, Irvine, CA (US); Dan M. Cooper, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 283 days.

(21) Appl. No.: 12/875,768

(22) Filed: Sep. 3, 2010

(65) Prior Publication Data
US 2011/0059476 A1 Mar. 10, 2011

Related U.S. Application Data (60) Provisional application No. 61/240,043, filed on Sep. 4, 2009.

(51) Int. Cl.
*C12M 1/107* (2006.01)
*C12M 3/00* (2006.01)
*C12M 1/21* (2006.01)

(52) U.S. Cl.
USPC .......... 435/300.1; 435/286.6; 435/287.5; 435/289.1; 435/304.1; 435/305.1; 435/307.1

(58) Field of Classification Search
USPC .......... 435/286.6, 287.5, 300.1, 289.1, 304.1, 435/305.1, 307.1
See application file for complete search history.

(56) References Cited

U.S. PATENT DOCUMENTS

| 2004/0203140 | A1* | 10/2004 | Akers et al. ............... 435/297.2 |
| 2005/0282269 | A1* | 12/2005 | Proulx ....................... 435/296.1 |
| 2005/0287660 | A1* | 12/2005 | Aubry et al. ............... 435/297.1 |
| 2008/0293135 | A1* | 11/2008 | Orr et al. ........................ 435/357 |
| 2009/0023194 | A1* | 1/2009 | Schmidt et al. ............ 435/173.1 |
| 2010/0076380 | A1* | 3/2010 | Hui ................................ 604/151 |
| 2011/0003390 | A1* | 1/2011 | Kudla ............................ 435/383 |
| 2012/0183987 | A1* | 7/2012 | Gevaert et al. ................. 435/29 |

OTHER PUBLICATIONS

Smith, David et al., Quantification of Acetaldehyde release by lung cancer cells in vitro using selected ion flow tube mass spectrometry, Rapid Commun. Mass Spectrum, 2003; 17: 845-850.

* cited by examiner

*Primary Examiner* — Nathan Bowers
(74) *Attorney, Agent, or Firm* — Vista IP Law Group LLP (57) ABSTRACT

A bioreactor for sampling the headspace above cells includes a glass reactor vessel having an interior space and a plurality of valves operatively coupled to the interior space of the glass reactor vessel. The bioreactor includes a sample holder configured to reside in the interior space. The interior space includes a charge of air with a known composition of volatile organic gases and, in some instances, doped with carbon dioxide. The sample holder may hold cells, bacteria, or viruses. The headspace may be sampled after incubation to determine the VOC content or content of specific VOC constituents. Examples include acetaldehyde and hexanaldehyde.

8 Claims, 11 Drawing Sheets

BIOREACTOR FOR QUANTIFICATION OF HEADSPACE VOC CONTENT FROM CULTURES

REFERENCE TO RELATED APPLICATION

This Application claims priority to U.S. Provisional Patent Application No. 61/240,043 filed on Sep. 4, 2009. The '043 Provisional Patent Application is incorporated by reference as if set forth fully herein.

STATEMENT REGARDING FEDERALLY SPONSORED RESEARCH OR DEVELOPMENT

This invention was made with Government support under Grant Nos. HD048721 and HL080947 awarded by the National Institutes of Health (NIH), and U54AI065359 awarded by the National Institute of Health (NIH)/National Institute of Allergy & Infectious Diseases (NIAID). The Government has certain rights in this invention.

FIELD OF THE INVENTION

The field of the invention generally relates to systems and devices (e.g., bioreactors) used for collecting and accurately quantifying trace amounts of volatile organic gases (VOCs) obtained from the headspace above cell cultures.

BACKGROUND OF THE INVENTION

It is known that useful information may be obtained using human exhaled breath biomarkers relevant to diseases ranging from cystic fibrosis and asthma to diabetes. Despite considerable efforts to understand the underlying cellular sources and determinants of exhaled compounds, knowledge of the underlying chemical and biochemical processes of exhaled gases remains limited in many cases. For example, cells may be collected and the headspace above the cells may be analyzed for gaseous products. However, the identification of gases in the headspace above cells growing in culture is not a simple task. Most of the gases of interest exist in concentrations so small that their accurate measurement can be a challenge (e.g. pptv to ppqv, $10^{-12}$ to $10^{-15}$).

The collection and measurement of these trace concentrations requires the fabrication of bioreactors which can accommodate a sufficient number of cells and can allow ready access to the culture medium and headspace for sampling gases with negligible ambient contamination. Prior studies utilized a glass bottle sealed with a septum to culture human lung cancer cells. Headspace gases were sampled by puncturing the septa with a hypodermic needle. A better design to capture and accurately measure headspace gases is needed.

SUMMARY

In one aspect of the invention, a bioreactor includes a glass reactor vessel having an interior space and a plurality of valves operatively coupled to the interior space of the glass reactor vessel. A sample holder is configured to reside in the interior space. The bioreactor contains a charge of air in the interior space with a known composition of volatile gases. In one optional aspect, the charge air is substantially free from VOCs. The charge air may also be doped with carbon dioxide (e.g., about 5% carbon dioxide based on volume).

In another aspect of the invention, the glass reactor vessel is made in two halves; a first glass half comprising an interior volume and a first valve communicating with the interior volume of the first glass half and a second glass half comprising an interior volume and a second valve communicating with the interior volume of the second glass half. A seal is interposed between the first glass half and the second glass half. The valves may be opened to purge the interior of the glass reactor vessel with air that that has a known composition of VOCs. This may be the same low VOC gas that is doped with carbon dioxide that is charged to the interior of the glass reactor vessel for incubation.

In still another aspect of the invention, a method is disclosed that includes placing a culture inside a glass bioreactor and purging the ambient air inside of the glass bioreactor. The inside of the glass bioreactor is charged with air with a known composition of volatile organic gases and, optionally, doped with 5% (by volume) carbon dioxide (commonly used for cell culture studies). In one aspect, the air is substantially free of VOCs although it is sufficient for the air to have a known composition of VOCs. The culture is then incubated for a period of time. A gas sample is then obtained from inside the glass bioreactor after incubation and the concentration of one or more chemical species is measured. The culture may contain cells, bacteria, or viruses. The chemical species (or individual chemical species) may serve as a fingerprint or signature for particular gases released by the cells, bacteria, or viruses. These signatures may then be used, for example, in testing to identify and monitor various disease or pathogenic states of a subject.

The method may be used to measure or quantify the headspace VOC content from cultures. The total VOC content or concentration may be determined. Alternatively, or in addition, the concentration of various VOC constituents may be determined. The culture sample may include human cells and in particular diseased human cells. Exemplary VOCs that can be quantified may include, for instance, acetaldehyde and hexanaldehyde. Of course, other chemical species may also be detected.

DETAILED DESCRIPTION OF THE ILLUSTRATED EMBODIMENTS

Figure 1A:
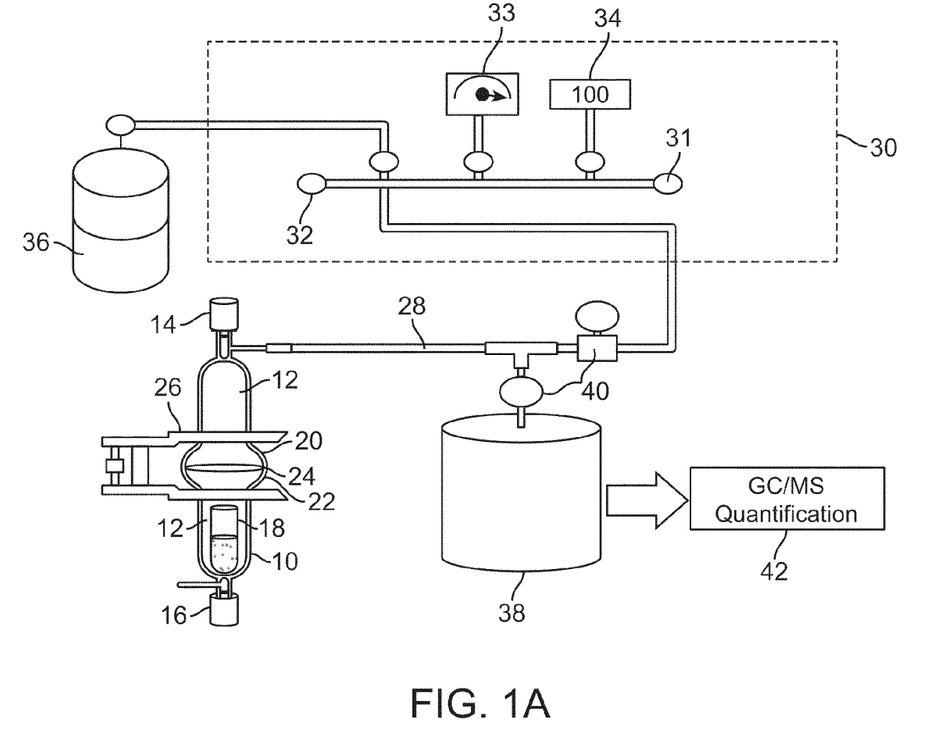
FIG. 1 illustrates a glass bioreactor according to one embodiment of the invention.

FIG. 1A illustrates a glass bioreactor 10 according to one embodiment of the invention. The glass bioreactor 10 includes an interior space 12 that isolated from the external environment. The interior space 12 may have a varying volume but as illustrated in FIG. 1A, the glass bioreactor 10 has an interior volume of 378 mL. As seen in FIG. 1A, there includes a first valve 14 and a second valve 16 that provide modulated access between the external environment and the interior space 12 of the glass bioreactor 10. As explained in more detail herein, one valve (either valve 14 or valve 16) may be used to evacuate gas from the interior space 12 while the other valve (the other of valve 14 and valve 16) may be used to introduce gas into the interior space 12. Of course, additional valves beyond valves 14, 16 illustrated in FIG. 1A may be used. The valves 14, 16 may include sealed valves such as high vacuum CHEM-VAC stopcocks as illustrated in FIG. 1A.

The glass bioreactor 10 includes a sample holder 18 contained in the interior space 12. The sample holder 18 is preferably removable from the interior space 12 and may include a vial or the like. The sample holder 18 preferably is made from a material that does not off gas volatile organic compounds (VOCs). Vials made from glass or polytetrafluoroethylene (PTFE) are examples of useful sample holders 18. As seen in FIG. 1A, the glass bioreactor 10 includes a first half 20 and a second half 22, each with their own interior space portion 12 that are joined together at a midline. A seal 24 such as an o-ring is interposed between the first half 20 and the second half 22. A clamp 26 such as a spherical joint THOMAS pinch clamp may be used to secure the two halves 20, 22 to one another.

Figure 1B:
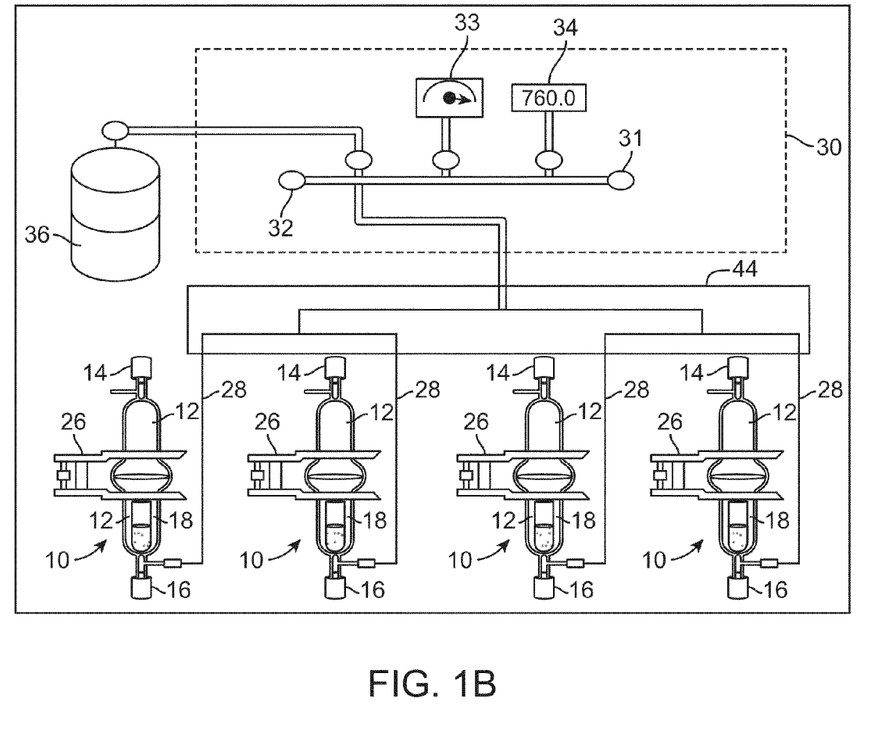

Non VOC-emitting tubing or other conduit 28 connects the valves 14, 16 to a pump system 30 as illustrated in FIGS. 1A and 1B. The pump system 30 includes a pump 31 that is used both to pump air into and out of the glass bioreactor 10. A vent 32 is provided in the pump system 30 that is used to evacuate. The pump system 30 further includes a thermocouple gauge 33 and a capacitance manometer 34 that are used to control pressure. The thermocouple gauge 33 is a high resolution pressure controller, detecting pressure in the range of 1 Torr to 0.01 Torr pressure. The pump system 30 is coupled to a source of charge gas 36. As explained herein, the charge gas 36 is preferably a low VOC-containing gas that is substantially free of VOCs. There is no absolute requirement that a low VOC-containing gas be used. Rather, the charge gas 36 needs to be a gas that has a known composition of VOCs. A charge gas 36 with low concentration of VOCs may be preferably because of the low concentration of VOC gas components that are produced by the test sample. In addition, the charge gas 36 may be doped with a certain amount of carbon dioxide such as 5% (by volume). The charge gas 36 may be pressurized using a pump or the like or the charge gas 36 may be contained in a tank or the like that can then be delivered to the glass bioreactor 10 via the manifold 30. The charge gas 36 may be obtained from ambient air having a known concentration profile of gases. One example of low VOC air is ambient air obtained from the rural Crooked Creek Research Station in California's White Mountains which has been studied extensively and has a known gas profile. Of course, the invention is not limited to low VOC air obtained from this location. Low VOC air may be obtained from other locations where the concentration profile is known or can be determined. The low VOC charge gas 36 may be also be manufactured or generated. For example, nitrogen, oxygen, and carbon dioxide may be combined in ratios similar to that found in ambient air (without VOCs) which may be used as artificially-created charge gas 36. Medical grade gas which has a known gas profile may be used, for example.

While low VOC air is preferred, in some instances, it may be possible to use a charge gas 36 that has some VOC content in the air. For example, if the constituents and concentration of various air components is known in advance it may still be possible to analyze headgas samples for the presence of VOCs created from incubating cultures. The problem is that the concentration of VOCs created from the culture during incubation are very small and it may be particularly difficult to measure changes in VOC concentrations with background levels of VOCs that are significantly higher than those created by the culture.

Still referring to FIG. 1A, a sample can 38 is shown coupled to conduit 28. The sample can 38 includes valves 40 such as a bellows valve that allows gas samples to be taken from the glass bioreactor 10. Gas from the sample can 38 is then input to a gas chromatograph/mass spectrometer 42 for quantification.

With reference now to FIG. 1B, in one embodiment, a manifold 44 is provided that offers the ability to run multiple glass bioreactors 10 simultaneously. For example, multiple glass bioreactors 10 may be coupled via conduits 28 to the manifold 44. In this regard, several different bioreactors 10 may run simultaneously. The manifold 44 is connected to the pump system 30 as described above.

HL60 Investigation

In this study, it was hypothesized that human immune cells in culture can generate detectable volatile organic compounds. HL60, a well-known promyelocytic human leukemia cell line was used as a model system in this study. The HL60 cells were grown in a limited, serum free medium as well as in fetal calf serum (often used in cell culture systems) in order to identify potentially confounding effects of gases likely evolved from the more complex media. A systematic approach was also used to determine contaminant gas signals (e.g., emanating from the medium, plastic culture ware, and ambient air) from signals whose source was the cells in culture.

Methods

Cell Culture

The HL60 cells were grown in RPMI 1640 (Gibco Ltd., Carlsbad, Calif., USA) supplemented with 10% fetal bovine serum (FBS) in a 37° C. incubator under 5% $CO_2$. The cells were transferred to the serum free media (AIM-V, Gibco Ltd., Carlsbad, Calif., USA) for up to 48 hours prior to the experiment to remove any conflicting growth factors provided by the FBS. On the day of the experiment, $40 \times 10^6$ cells were added to 30 ml of fresh culture medium in Teflon vials (Nalgene, Rochester, N.Y., USA).

Headspace Gas Collection Equipment and Methods

The Teflon vials 18 containing the cell suspensions ($40 \times 10^6$ cells/30 ml) were placed inside cylindrical glass bioreactors 10. The glass bioreactors 10 were specifically designed to collect the gaseous headspace above aqueous cultures as explained herein with respect to FIGS. 1A and 1B. The glass bioreactor 10 consisted of two glass halves 20, 22 joined together with an o-ring seal 24 and secured by a spherical joint THOMAS pinch clamp 26. The glass bioreactor 10 had an interior volume of 378 mL and was fitted with valves, sealed with high vacuum CHEM-VAC stopcocks 14, 16, at both ends. Once the apparatus was fully assembled it was attached to a pump system 30 to purge the glass bioreactor 10 of ambient air and replace it with air containing low levels of volatile organic compounds (VOCs) and 5% $CO_2$. The low VOC air was prepared by doping 5% pure $CO_2$ into whole air collected by the Blake-Rowland lab from the rural Crooked Creek Research Station in California's White Mountains. Of course, as explained herein, other sources of air both natural and artificial may be used.

FIGS. 2A, 2B, 4A, 4B illustrate the low levels of selected VOCs in the collected air as compared to the headspace samples of the media and HL60 samples. The manifold 44, which was equipped with an Edwards Model vacuum pump 31 and a 10,000 torr Edwards capacitance manometer 34, was capable of purging numerous bio-reactors 10 simultaneously as seen in FIG. 1B. A needle valve (Swagelok, Solon, Ohio) and flowmeter (Dwyer Instruments Inc. Michigan City, Ind., USA) was used to adjust the net flow to the glass bioreactors 10 to 2500 cc/min. The purge time was adjusted, depending on the number of bioreactors 10 in use, to ensure that each bioreactor 10 was flushed with a volume of air approximately three times that of its own. After purging was completed, the stopcocks 12, 14 on each glass bioreactor 10 were sealed at ambient pressure.

The glass bioreactors 10 were then placed in an incubator at 37° C. for the desired amount of time. After incubation, ¼" stainless steel flex tubing 28 was used to connect the glass bioreactor to a stainless steel canister 38 (Swagelok, Solon, Ohio). The tubing 28 was evacuated to $10^{-1}$ torr and then isolated and the evacuated canister's 38 Swagelok metal bellows valve 40 was opened. The Teflon stopcock 14 to the bioreactor 10 was opened and the system was allowed to equilibrate for one minute. The canister 38 was then closed via valve 40, thereby isolating and preserving a portion of the bioreactor's headspace.

Following sample collection the bioreactor 10 was disassembled and the cells were immediately collected and counted. To minimize the confounding effects of trace gases in the ambient air or from the incubated plastic culture ware, ambient room air samples were collected during purging and transfer of the headspace of the bioreactor 10. Plastic cell culture ware and the Teflon vials were also examined as potential sources of contamination.

Gas Chromatography-Mass Spectrometry

The analyses of the headspace gases and room samples were performed using a gas chromatograph/mass spectrometer 42. A complete description of the GC parameters and analytical methods are fully discussed, for instance, in Colman J J, Swanson A L, Meinardi S, Sive B C, Blake D R, Rowland F S: Description of the analysis of a wide range of volatile organic compounds in whole air samples collected during PEM-tropics A and B. Anal Chem 2001, 73:3723-3731, which is incorporated by reference as if set forth fully herein. Briefly, a 233 $cm^3$ (at STP) sample is cryogenically pre-concentrated and injected into a multi-column/detector gas chromatography system. The system consists of three Hewlett-Packard 6890 gas chromatography (GC) units (Wilmington, Del., USA) with a combination of columns and detectors capable of separating and quantifying hundreds of gases, including but not limited to, non-methane hydrocarbons (NMHC), alkyl nitrates and halocarbons in the ppm to ppq range ($10^{-6}$ to $10^{-15}$). Nitrogen oxides, ammonia and hydrogen sulfide are not quantified with this analytical system. Preliminary identifications of the unknown signals were made using GC-MS ion fragmentation matching software (Agilent Technologies, Santa Clara, Calif., USA). Verification was obtained by injecting the headspace of pure compounds (diluted to ppb levels with purified UHP helium) to ensure the elution time matched that of the unknown. The mixing ratios of the oxygenates were determined using effective carbon numbers (ECN) and the linear response to carbon number of the FID, which is accurate to within 25%. Concentrations of $CO_2$ in the bioreactors following incubation were determined using a separate gas chromatography system. Aliquots of the collected headspace gas were injected onto a Carbosphere 80/100 packed column output to a thermal conductivity detector (TCD).

Helium Stripping

Helium stripping was used in an attempt to purge less volatile gases from the cell culture media. After 48 hours incubation, the headspace above the HL60 cells and the media was collected. The Teflon vial 18 was removed from the bioreactor 10 and the cells were collected and counted. The supernatant was poured into a new Teflon vial and placed back into a bioreactor. The headspace of the bioreactor 10 was then flushed for five minutes with purified ultra high purity (UHP) helium (Matheson, Newark, Calif., USA). Helium was bubbled through the media and collected in an evacuated ($10^{-2}$ Torr) 1.9 L stainless steel canister 38 to a final pressure of 900 Torr. The procedure was repeated identically for the media-only condition.

Statistics

Experiments were repeated at least three times for gas phase measurements. A 2-way analysis of variance (ANOVA) was applied to compare the gas component emitted at three incubation times (4 hour vs. 24 hour vs. 48 hour) from different conditions of cell culture (media only, and HL60 cells). Data presented are mean±standard deviation (SD) and the significance level was set at level 0.05. Multiple comparisons adjustment was applied using Bonferroni's method.

Results

Figure 2A:
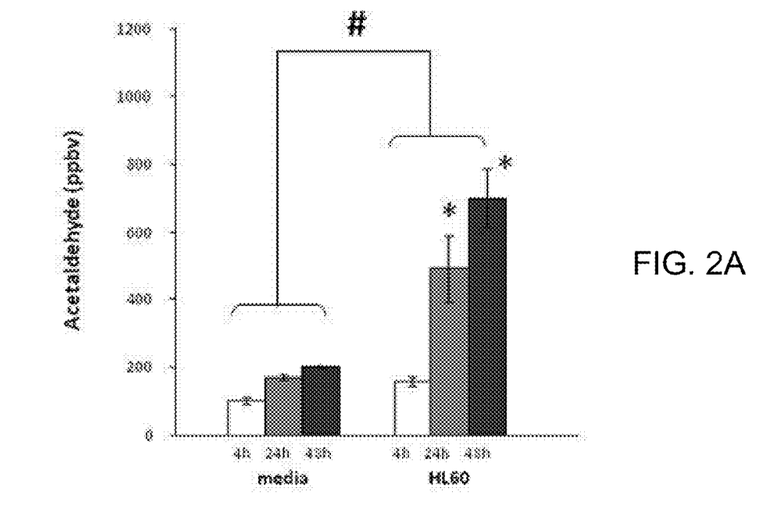
FIG. 2A illustrates the mean+/−SD acetaldehyde concentration in the bioreactor headspace of media and HL60 cells at 4 hours (empty bar), 24 hours (gray bar), and 48 hours (black bar) of incubation.

The most prominent and reproducible signal from HL60 culture was acetaldehyde. FIG. 2A illustrates a significantly increased emission ($p<0.0001$) of acetaldehyde at 24 hours and 48 hours compared to 4 hours from HL60 cells (4-h 157±13 ppbv, 24-h 490±99 ppbv and 48-h 698±87 ppbv), but not from the control such as media (4-h 100±9 ppbv, 24-h 170±8 ppbv and 48-h 202±1 ppbv). The elevated acetaldehyde observed for the HL60 was significantly higher when compared with media ($p<0.0001$). Significantly different levels of acetaldehyde are emitted at 24 hour and 48 hour incubations compared to 4 hours from HL60 cells (4-h 157±13 ppbv, 24-h 490±99 ppbv and 48-h 698±87 ppbv). The symbol (*) represents concentrations significantly higher compared to 4 hours from HL60 cells, and the symbol (#) represents significantly higher acetaldehyde generation from HL60 cells compared to media.

Figure 2B:
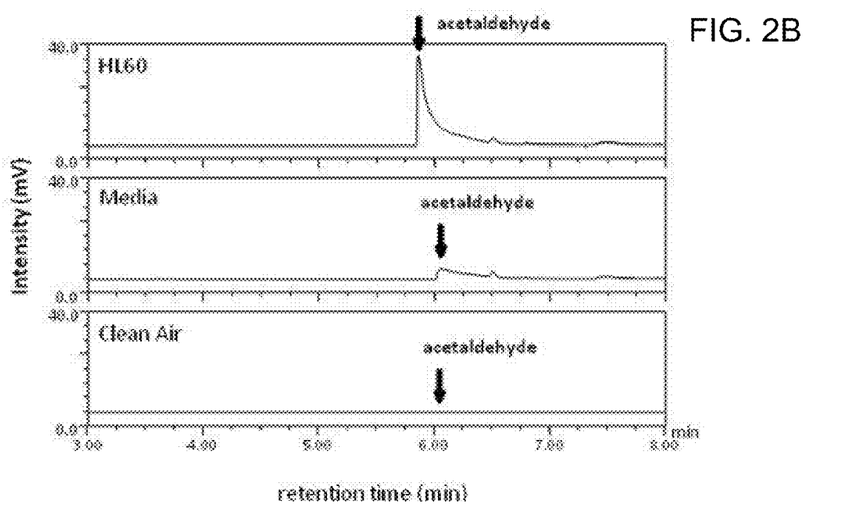
FIG. 2B illustrates representative chromatograms of acetaldehyde after 48 hours of incubation. Low VOC air was used to flush the headspace of the bioreactors containing vials of media and HL60 prior to incubation.
Figure 3:
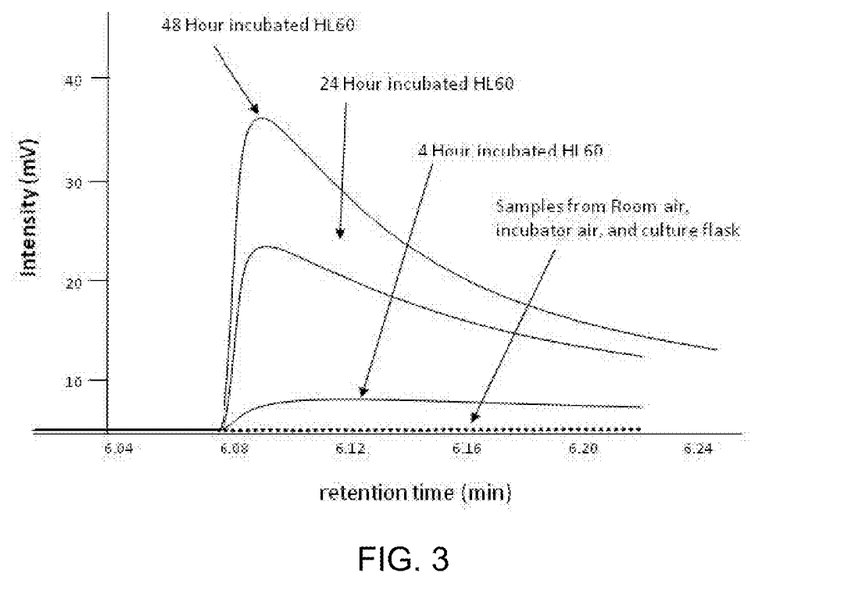
FIG. 3 is a chromatogram of acetaldehyde from the bioreactor headspace of cells 4, 24, and 48 hour incubations and ambient lab air.

FIG. 2B illustrates the insignificant levels of acetaldehyde in all other controls (i.e., room samples, empty Teflon vial, and empty culture flasks). FIG. 3 is a representative chromatogram illustrating the time-dependent increase of acetaldehyde concentration in the headspace above the HL60 cells. The asymmetry of the acetaldehyde peak is a result of the oxygenate's interaction with the column, canister and manifold. Its slower desorption from the active sites of these surfaces leads to the observed tailing. The asymmetry is not observed in hexanaldehyde as its behavior is dominated by its longer hydrophobic carbon tail.

Figure 4A:
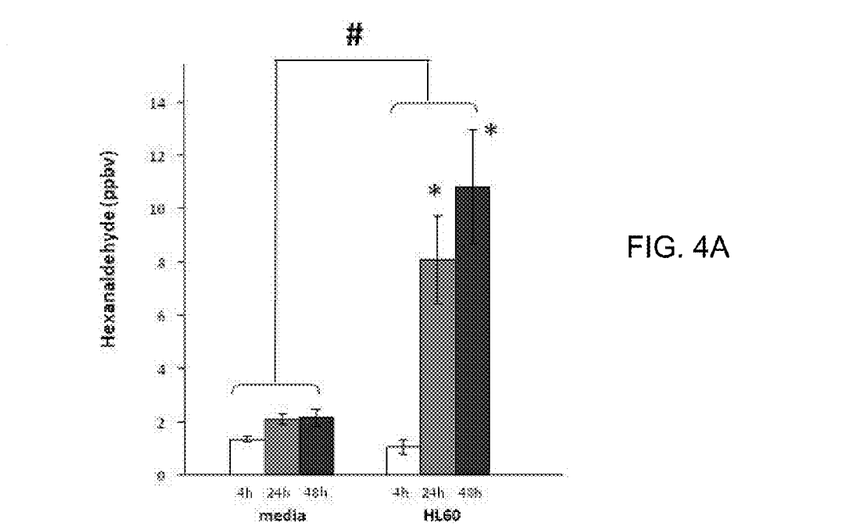
FIG. 4A illustrates the mean+/−SD hexanaldehyde concentration in the bioreactor headspace of media and HL60 cells at 4 hours (empty bar), 24 hours (gray bar), and 48 hours (black bar) of incubation.
Figure 4B:
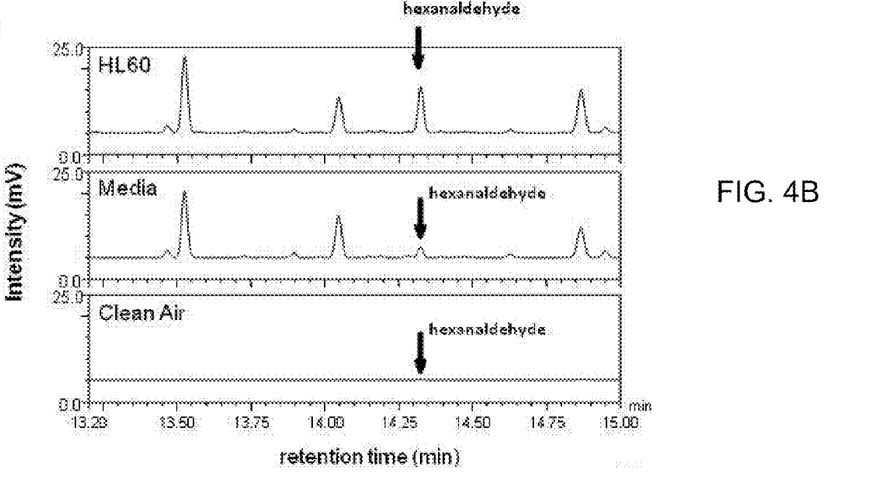
FIG. 4B illustrates representative chromatograms of hexanaldeyde after 48 hours of incubation. The low VOC air was used to flush the headspace of the bioreactors containing vials of media and HL60 prior to incubation.
Figure 5:
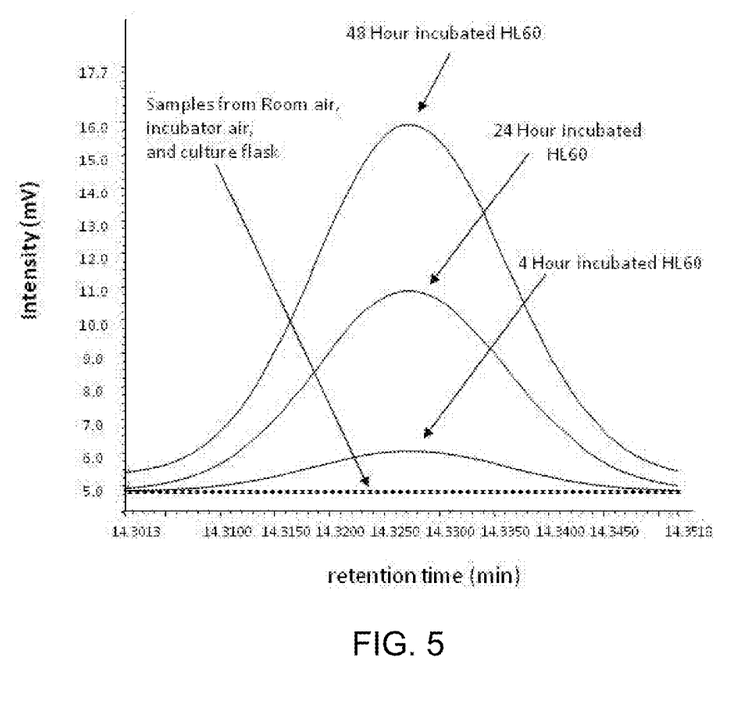
FIG. 5 is a chromatogram of hexanaldehyde from the bioreactor headspace of HL60 cells from 4, 24, and 48 incubations and ambient air.

Hexanaldehyde was also observed to significantly increase ($p<0.0001$) at 24 hours and 48 hours relative to 4 hours in HL60 cells (4-h 1±0.3 ppbv, 24-h 8±2 ppbv and 48-h 11±2 ppbv) but not in the media (4-h 1±0.1 ppbv, 24-h 2±0.2 ppbv and 48-h 2±0.3 ppbv). The elevated hexanaldehyde observed for the HL60 cells was also significantly higher when compared to media ($p<0.0001$) as seen in FIGS. 4A and 5. As seen in FIG. 4A, headspace hexanaldehyde concentration is significantly higher from HL60 cells compared to media ($p<0.0001$). Significantly different levels of hexanaldehyde are emitted at 24 hour and 48 hour incubations compared to 4 hours from HL60 cells (4-h 1.1±0.3 ppbv, 24-h 8.1±1.7 ppbv and 48-h 10.8±2.2 ppbv). The symbol (*) represents concentrations significantly higher compared to 4 hours from HL60 cells, and the symbol (#) represents significant higher hexanaldehyde generation from HL60 cells compared to media.

Hexanaldehyde was not present in appreciable concentrations in any of the identified sources of contamination such as plastic culture ware, room air samples, and incubator air samples. This can be seen from the "Media" and "Clean Air" graphs of FIG. 4B. FIG. 5 is a chromatogram of hexanaldehyde from the bioreactor 10 headspace of HL60 cells from 4 hour, 24 hour, and 48 hour incubations. Also included as a control were samples from room air, incubator air, and culture flask. Hexanaldehyde was not present in appreciable concentrations in any of the identified sources of contamination such as Teflon vials, plastic culture ware, room air samples, and incubator air samples.

Among numerous headspace gases detected from the current HL60 study, acetaldehyde and hexanaldehyde were the only gases found in appreciable amounts from HL60 cells. In addition, no additional gases were observed when the media was stripped with helium. As expected acetaldehyde and hexanaldehyde were still found in higher concentrations when stripped from the media in which the cells were cultured (531 ppbv and 6 ppbv, respectively) compared to the control media in which no cells were grown (126 ppbv and 2 ppbv, respectively).

Figure 6:
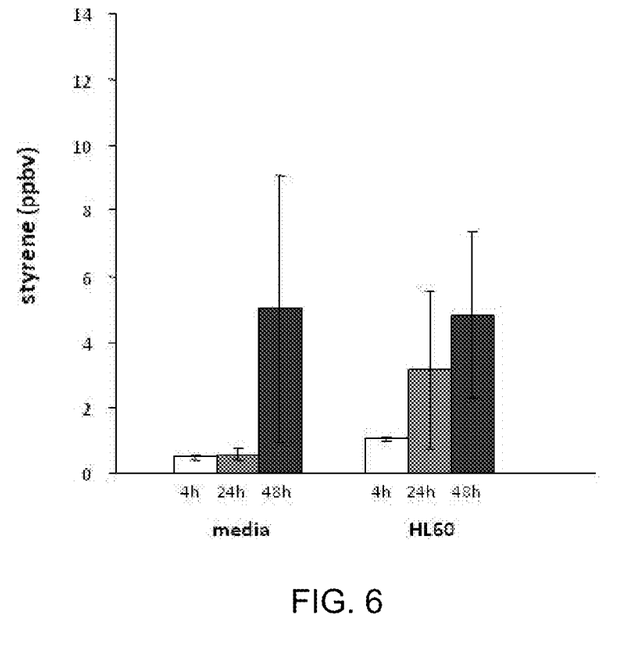
FIG. 6 illustrates the mean+/−SD styrene concentration in the bioreactor headspace of media and HL60 cells at 4 hours (empty bar), 24 hours (gray bar), and 48 hours (black bar) of incubation. Styrene is an example contaminant, which originates from the cell culture flask in which the HL60 cells are grown.

HL60 cell viability decreased with incubation time. Percent survival for the HL60 cells was 93±4%, 96±4%, and 70±6% for 4 hour, 24 hour, and 48 hour incubations respectively. Interestingly, several observed gas signals that increased with incubation time were later identified to be contaminants of the plastic culture ware or carry over from the fetal calf bovine serum. Styrene and 4-methyl-2-pentanone are examples of contamination. FIG. 6 illustrates that styrene was seen in the samples containing HL60 cells, and media. However, the cell culture flasks in which the HL60 cells were grown were found to emit styrene. In general, styrene responses fluctuated greatly and are assumed to be due to the various ages and exposures of the different plastic culture-ware and containers in which reagents were stored. The second contaminant was 4-methyl-2-pentanone. This compound was found in the ambient room air, and the headspace of media containing 10% of FBS, which was then believed to be carried over into the samples containing cells to a significant but lesser extent. Acetaldehyde and hexanaldehyde were not observed to outgas from the plastic culture ware.

Discussion

It was found that HL60 cells generate appreciable amounts of acetaldehyde and hexanaldehyde that could be detected in the head-space above the culture media. Moreover, the experimental procedure was refined so that reproducibility of gas profiles from the cells could be observed.

Acetaldehyde has previously been detected in the exhaled human breath, and in human lung cancer cell line cultures. The current experimental data demonstrate that human white blood cell line, HL60 is also capable of producing acetaldehyde. When compared to the previously reported lung cancer cell line, SK-MES, HL60 produced similar amounts of acetaldehyde in the headspace (16-h 408±191 ppbv; 24-h 490±99 ppbv for 40 million of SK-MES and HL60, respectively). Until fairly recently, it was believed that acetaldehyde in human cells was produced predominately from hepatic ethanol metabolism by the enzyme alcohol dehydrogenase. Previous studies have demonstrated that human blood cells also metabolize ethanol to acetaldehyde or oxidize it further to acetate in an alcohol dehydrogenase-independent manner. Work by Hazen and colleagues from about ten years ago confirmed the ability of neutrophils to oxidize amino acids and produce aldehydes, a reaction requiring myeloperoxidase (MPO), hydrogen peroxide ($H_2O_2$), and chloride ion ($Cl^-$). Because HL60 cells have high myeloperoxidase protein expression and activity, this amino acid oxidation is likely an alternative pathway for the generation of acetaldehyde from at least HL60 cells.

Hexanaldehyde has previously been detected in the exhaled breath, bronchial lavage fluid following ozone exposure, and exhaled breath condensate of healthy human volunteers and chronic obstructive pulmonary disease (COPD) patients. Recently, elevated hexanaldehyde has been detected in whole blood from lung cancer patients compared to the healthy controls. However, a cellular source of hexanaldehyde has not been completely identified. Oxidation of omega-6 unsaturated fatty acids (i.e., linoleic acid, arachidonic acid) has been reported to generate hexanaldehyde in rat and human bronchial lining fluids, and is accepted as the most plausible cellular source of hexanaldehyde. Human neutrophils are able to generate ozone as a part of their phagocyte activity. Thus, it is speculated that part of the observed hexanladehyde from HL60 cells originates from the cellular reaction between cellular fatty acid and ozone.

With the exception of acetaldehyde and hexanaldehyde, all other gases quantified in the headspace of the HL60 cells were either near the detection limit of the GC-MS system 42, or were evolved solely from the media (i.e., pentanaldehyde). In addition, styrene was identified as a contaminant emanating from the plastic culture ware and was excluded as seen in FIG. 6.

Helium stripping is a commonly used method to detect less volatile gases dissolved in media. The purpose of helium stripping in this study was to identify gases generated by HL60 cells that would not be present in the head-space because of low volatility. However, no additional gases were observed from stripping the media with helium. This result further confirms our finding that acetaldehyde and hexanaldehyde are the major gases evolved from HL60 culture.

Interest in using exhaled gases as non-invasive markers in clinical diagnostics and therapeutic monitoring has steadily increased. In parallel, considerable efforts have been taken to understand the underlying source and determinants of exhaled volatile gases. The current study demonstrates that acetaldehyde and hexanaldehyde might be useful to identify the presence of innate immune cells like neutrophils. Moreover, these gases may also have biological importance beyond their possible role as biomarkers. For example, acetaldehyde, a known lung irritant, can influence blood coagulation and induce histamine release. The fact that these gases might be produced endogenously by neutrophils leads to the speculation that some of the deleterious effects associated, for example, with pneumonia (characterized by aggregation of neutrophils in the lung) may be due, in part, to the production of these gases by the leukocytes themselves.

Neutrophil and PBMC Investigation

In this investigation, it was hypothesized that human primary leukocytes (i.e., neutrophils and peripheral blood mononuclear cells (PBMCs)) could generate detectable levels of cell type-specific gasses. The glass bioreactor 10, in conjunction with the equipment and techniques described herein for collecting and analyzing the cell culture's headspace, provide detection limits of parts-per-billion and for some compounds in the parts-per-trillion. The goals of the current study were included (1) to examine the adaptability of the glass bioreactors 10 and the analytical techniques using primary human leukocyte cells in culture; and (2) to identify unique gas signatures, should they exist, from two categories of leukocytes: neutrophils and PBMCs.

Methods

Ten healthy, adult men between the ages of 18 and 65 years of age participated in this study through the Institute for Clinical Translational Sciences (ICTS) general blood donor program. Subjects having a history of any chronic medical conditions, or use of any medications were excluded from the study. Blood from the participants was sampled from the antecubital vein using EDTA-treated vacutainers. Neutrophils and PBMCs were then isolated using OptiPrep Density Gradient Medium (Sigma). Standard and consistent isolation practices were used to minimize any potential changes due to manipulation of neutrophils and PBMCs. The isolation of the neutrophils and PBMCs consistently yielded≥98% purification based on Wright stain and Flow Cytometric analysis.

Purified neutrophils and PBMCs were re-suspended in RPMI 1640 (Irvine Scientific, Santa Ana, Calif.) and supplemented with 10% fetal calf serum (FCS). The vials containing cell suspensions (30×106 cells/10 mL) were placed inside glass bioreactors 10 which were specifically designed to collect the gaseous headspace above aqueous cultures. To minimize ambient contaminants each glass bioreactor 10 was flushed with air containing low levels of VOCs and 5% $CO_2$ for ten minutes at 125 mL per minute. The glass bioreactors 10 were then placed in an incubator at 37° C. for 24 hrs. The headspace was collected after incubation and its composition was analyzed by a gas chromatography system 42 with multiple columns and multiple detectors as seen in FIG. 1A. Following sample collection, the bioreactor was disassembled and the cells were immediately collected and counted. Trypan blue exclusion assay was performed to determine the percentage of live cells following incubation.

The analyses of the headspace gases was then performed as outlined previously. Generally, a 233 $cm^3$ (at STP) sample was cryogenically pre-concentrated and injected into a multi-column/detector GC/MS system 42. The GC/MS system 42 consists of three Hewlett-Packard 6890 GC units (Wilmington, Del.) using a combination of columns and detectors capable of separating and quantifying hundreds of gases, including, but not limited to, non-methane hydrocarbons (NMHC), alkyl nitrates and halocarbons below pptv ($10^{-12}$). The detectors include flame ionization detectors (FIDS), electron capture detectors (EGDs), and a mass spectrometer detector (MSD). Preliminary identifications of the unknown signals were made using GC-MSD ion fragmentation matching software (Agilent Technologies, Santa Clara, Calif.). Verification was obtained by injecting the diluted headspace of pure compounds (Sigma-Aldrich, St. Louis, Mo.) to ensure that the elution time matches that of the unknown. The percent $CO_2$ in the air used to flush the bioreactors was determined using a Carbosphere 80/100 packed column output to a thermal conductivity detector (TCD).

From each of the ten samples of neutrophils, PBMCs, and corresponding media, the gases were obtained with or without replicates depending on the availability of blood or media, and the average was calculated for each gas if there were replicates. The gases whose maximum expression from all samples was less than 100 pptv and/or whose maximum change, increase or decrease, from media was less than 50% were excluded for further analysis. The remaining gases from neutrophils and from PBMCs were compared to the corresponding media using the Wilcoxon signed-rank test. Due to the large number of gases under investigation, we further applied Benjamini and Hochberg's False Discovery Rate controlling method to adjust for multiple comparisons. A gas from neutrophils or PBMCs is considered significantly changed from the media if FDR<0.05. All analysis was done with SAS 9.2 (Cary, N.C.) and data are presented with median and range (minimum, maximum).

Results

A total of fifty nine gases were obtained from human neutrophils (n=10, total replicates=20) and PBMCs (n=10, total replicates=28) and media control (n=10, total replicates=22), of which 24 gases were used for statistical analysis. To exclude gases originating from other than cells, the experiments included the analyses of various control conditions such as ambient room air, incubator air, headspace gas from empty flushed and incubated bioreactors 10, headspace gas from empty EDTA-treated vacutainers, and headspace gas from incubated density gradient solutions used for leukocyte separation. After multiple comparison adjustment, six gases (acetaldehyde, hexanaldehyde, iso-propylbenzene, chloroethane, 3-methylpentane, methylcyclopentane,) from both neutrophils and PBMCs, three gases (n-hexane, styrene, 2-methyl-2-butene) from only PBMCs, and one gas (ethylene sulfide) from only neutrophils were found significantly different from media.

Figure 7A:
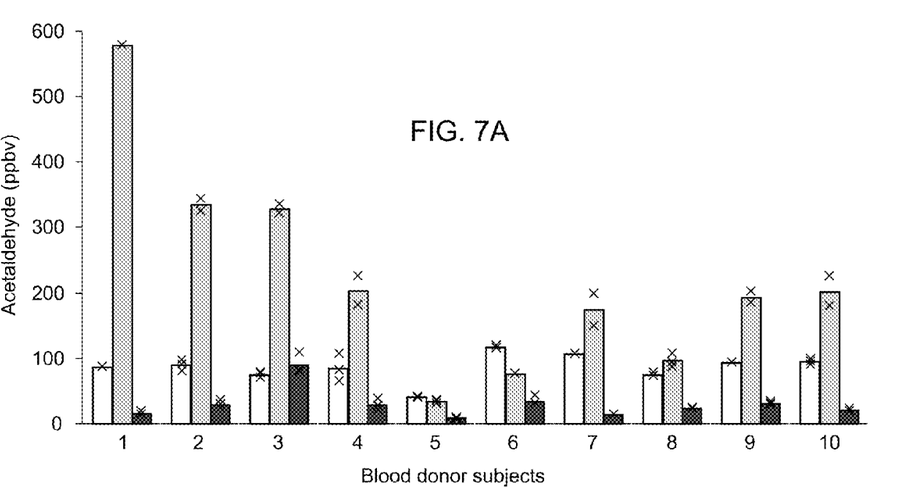
FIG. 7A illustrates a graph of the acetaldehyde emitted in the bioreactor headspace of neutrophils (middle bar) and PBMCs (right-most) following 24 hours of incubation. Culture media is left-most graph.
Figure 7B:
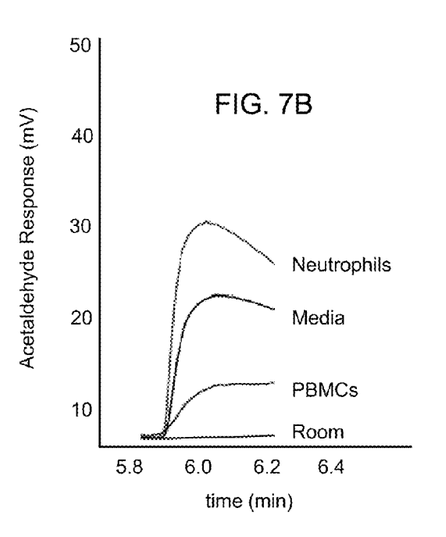
FIG. 7B illustrates representative chromatograms of acetaldeyde from neutrophils, PBMCs, and culture media. Acetaldehyde has been generated from neutrophils, however, PBMCs from the same subject presented a level below the culture medium.
Figure 7C:
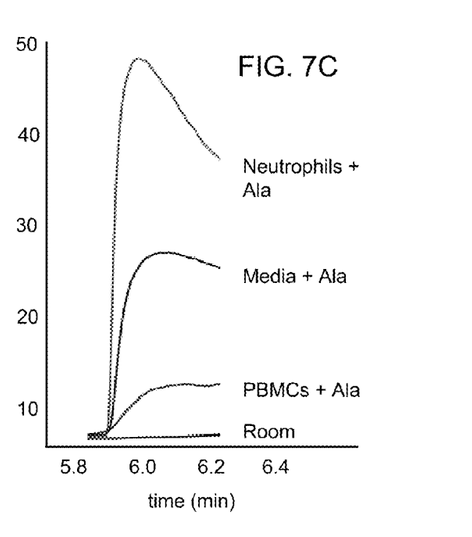
FIG. 7C illustrates representative chromatograms of acetaldeyde in the presence of an additional 100 mg/L alanine. Neutrophils cultured with an additional alanine emitted greater than 1.4 fold higher amounts of acetaldehyde when compared to the acetaldehyde cultured in basal medium. PBMCs from the same subject presented a level below the culture medium even in the presence of alanine.

Primary human neutrophils and PBMCs produced several distinct gas signatures that were significantly different from media control. FIG. 7A illustrates a significantly increased emission of acetaldehyde from cultured neutrophils isolated from ten healthy blood donors (median (min, max); 197 (34, 577) ppbv) when compared with media alone (88 (40,116) ppbv, p=0.014, FDR=0.038). Interestingly, the level of acetaldehyde from PBMCs obtained from the same subject was 26 (8, 89) ppbv, significantly below media alone (p=0.004, FDR=0.015). An overlay of representative chromatograms of acetaldehyde from neutrophils, PBMCs, and culture media are presented in FIG. 7B. The concentration of acetaldehyde in the headspace of the neutrophil culture was greater than the culture medium. However, the headspace of PBMCs cultured from the same subject had concentrations of acetaldehyde below the culture medium. As described elsewhere the tailing peak is due to the oxygenate's interaction with the surfaces and column of the analytical system. Neutrophil cells emitted greater than 1.4 fold higher amounts of acetaldehyde in the presence of an additional 100 mg/L alanine. In contrast, the addition of alanine did not make any changes in acetaldehyde released from cultured PBMCs (FIG. 7C).

Three other gases were observed to decrease in the headspace above both neutrophils and PBMCs. Hexanaldehyde was 3.5 (1.0, 6.8) ppbv from media, but was only 0.8 (0.4, 2.5) ppbv from neutrophils (p=0.002, FDR=0.011) and 0.5 (0.2, 0.8) ppbv from PBMCs (p=0.002. FDR=0.011); iso-propylbenzene was 161 (58,278) ppbv from media, but was only 104 (18,156) ppbv from neutrophils (p=0.002, FDR=0.011) and 85 (42,142) ppbv from PBMCs (p=0.002 FDR=0.011); and chloroethane ($CH_3CH_2Cl$) was 5.0 (1.6, 13.3) ppbv from media, but was only 3.5 (1.4, 7.9) ppbv from neutrophils (p=0.014, FDR=0.038) and 3.0 (1.1, 6.3) ppbv from PBMCs (p=0.004, FDR=0.015). The decrease in concentration of these gases may be due to removal by cellular metabolism. Hexanaldehyde, isopropylbenzene, and chloroethane concentrations from neutrophils and PBMCs in culture obtained from the ten donors and representative chromatograms are presented in FIG. 8.

Figure 10:
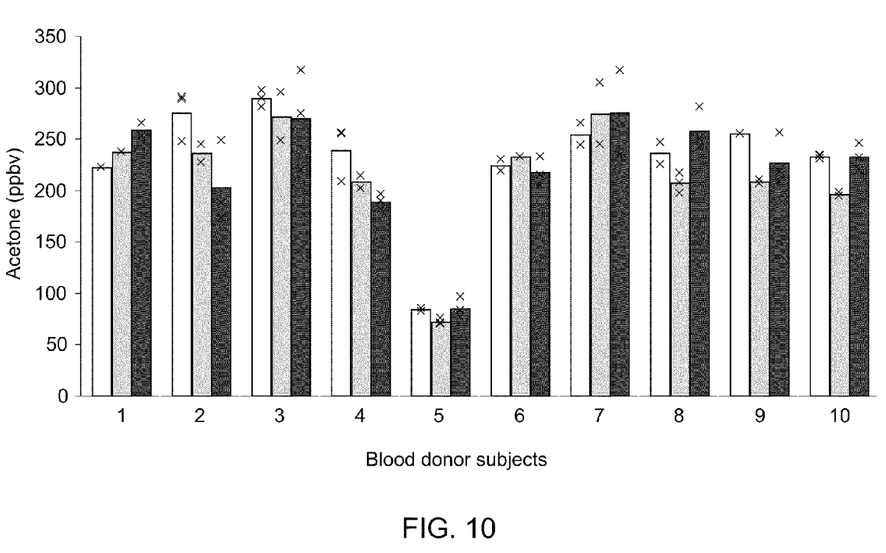
FIG. 10 illustrates the acetone concentration emitted in the bioreactor headspace of neutrophils (middle bar) and PBMCs (right-most bar) following 24 hours of incubation. The right-most bar represents the media only. The symbol "X" represents replicates. The emitted acetone concentrations from cell culture bioreactors in which the neutrophils and PBMCs were grown were not different from the headspace gases obtained in the media only.

Ethylene sulfide was 1.4 (0.3, 9.1) ppbv from media, the level was significantly lower (p=0.0098, FDR=0.033) from neutrophils 0.6 (0.1, 2.0) ppbv but not from PBMCs 1.8 (0.1, 4.6) ppbv (data not shown). Several gases were initially observed to be significantly higher from PBMCs and/or neutrophils in culture. However, these gases turned out to be carry-over contaminants originating from the plastic EDTA vacutainers used to collect the whole blood or from the plastic tubes used to separate cells. These gases include methylcyclopentane, 3-methylpentane, and n-hexane as shown in FIG. 10, and 2-methyl-2-butene and styrene not shown.

The cell viability or percent survival for the neutrophils and PBMCs was 95±18% and 76±18% respectively. Neutrophils, as expected, were not as robust as the PBMCs and their population was reduced following 24 hr incubation.

Discussion

The neutrophil and PBMC Investigation demonstrates that human primary immune cells produce volatile gases that can be measured in vitro in trace amounts. Further, the method enables the ability to detect basal levels of acetaldehyde produced by unperturbed cultured neutrophils. The data further suggest that different leukocyte subtypes have different gas profiles.

Acetaldehyde has previously been detected in the exhaled human breath and in human lung cancer cell line cultures. In general, acetaldehyde concentrations were found to be taken up by lung cancer cell lines and normal lung cell lines. The current study also demonstrates that primary myelocytic cells, i.e., neutrophils obtained from healthy subjects, emitted appreciable amounts of acetaldehyde into the gas phase, above the background media acetaldehyde levels. However, healthy human PBMC culture, by an unknown mechanism, tends to consume acetaldehyde rather than release it into the gas phase. The acetaldehyde released from cultured cells appears to be cell type-specific (i.e., neutrophil-type v. PBMC-type). Work by Hazen and colleagues confirmed the ability of PMA-activated neutrophils to oxidize amino acids and produce aldehydes, a reaction requiring myeloperoxidase (MPO), hydrogen peroxide ($H_2O_2$), and chloride ion ($Cl^-$). Since human neutrophils have high myeloperoxidase protein expression and activity, this amino acid oxidation is a likely pathway for the generation of acetaldehyde from at least neutrophils. In agreement with Hazen, when the amino acid alanine was added to the culture system, acetaldehyde release from neutrophils in culture increased as seen in FIG. 7C. However, the addition of alanine did not alter acetaldehyde emission from PBMCs in culture. The precise mechanism of acetaldehyde metabolism by PBMCs has not yet been fully investigated.

Figure 8A:
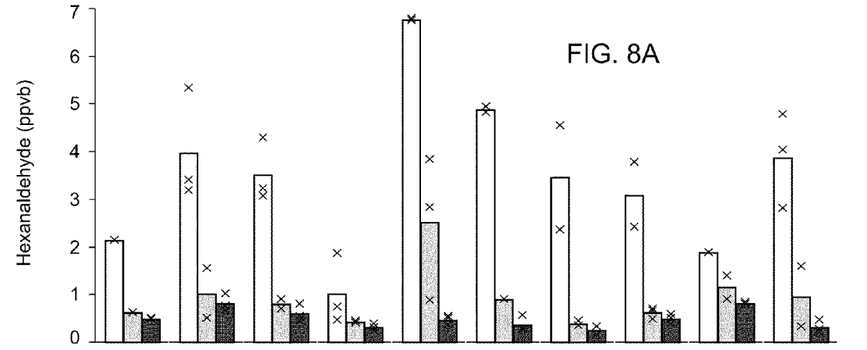
FIG. 8A illustrates the concentration of hexanaldehyde emitted in the bioreactor headspace of neutrophils (middle bar) and PBMCs (right bar) following 24 hours of incubation. White bars (left most) represent culture medium.
Figure 8B:
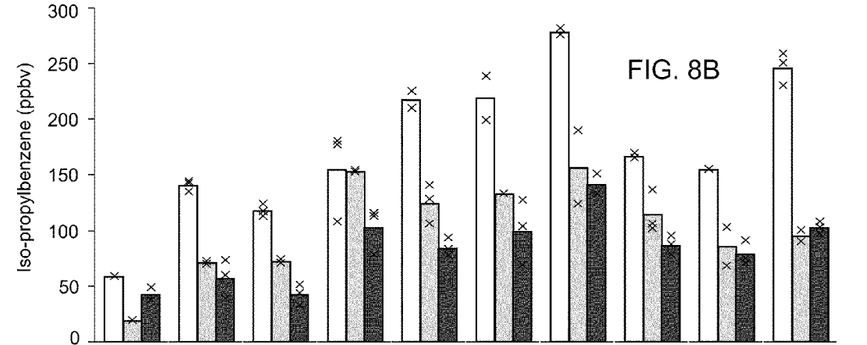
FIG. 8B illustrates the concentration of isopropylbenzene emitted in the bioreactor headspace of neutrophils (middle bar) and PBMCs (right bar) following 24 hours of incubation. White bars (left most) represent culture medium.

Intriguingly, the current investigation suggests that both primary neutrophils and PBMCs appear to metabolize hexanaldehyde (FIG. 8A). The cellular mechanisms of hexanaldehyde metabolism by human primary neutrophils and/or PBMCs require further investigation. Further, certain bacteria (i.e., *Pseudomonas putida* RE 204) have the ability to catabolize isopropylbenzene, and thus, have been suggested as a bioindicator of hydrocarbon pollution in the environment. However, the cellular metabolism of isopropylbenzene in human immune cells like neutrophils and PBMCs has not been previously observed. This investigation may suggest, in part, that human immune cells are capable of metabolizing isopropylbenzene (FIG. 8B).

Figure 8C:
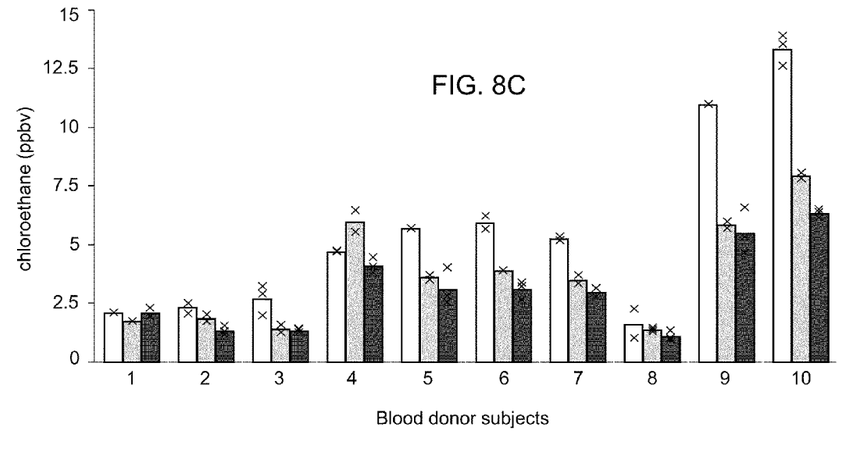
FIG. 8C illustrates the concentration of chloroethane emitted in the bioreactor headspace of neutrophils (middle bar) and PBMCs (right bar) following 24 hours of incubation. White bars (left most) represent culture medium.
Figure 9:
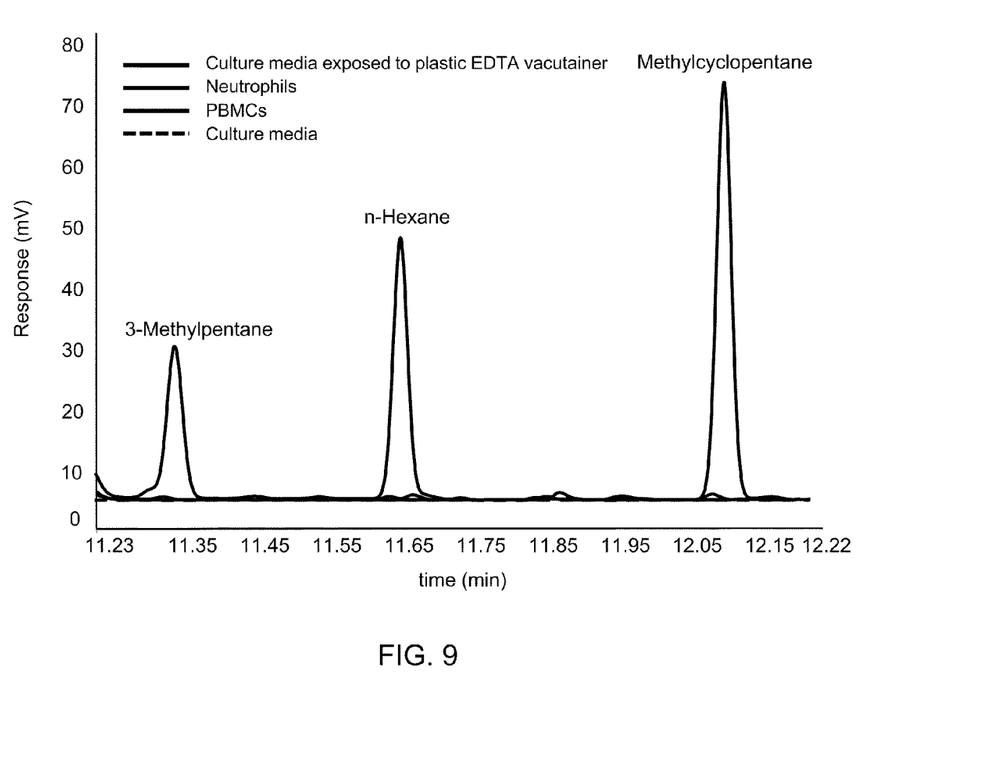
FIG. 9 illustrates representative chromatograms of media (dashed) and media exposed to plastic EDTA vacutainers. The gases comprising 3-methyl pentane, n-hexane, methylcyclopentane, and 2-methyl-2-butene (not shown) were observed to be significantly higher from PBMCs and/or neutrophils in culture. However, the gases were determined to likely be carry-over contaminants from the plastic EDTA vacutainers, and excluded from the study.

Chloroethane ($CH_3CH_2Cl$) was observed to be taken up by both neutrophils and PBMCs as seen in FIG. 8C. Chloroethane can be eliminated from the body either by breath exhalation or cellular oxidation. The precise mechanism of human leukocyte catabolism of chloroethanes remains unknown. However, current observation may suggest, in part, that human leukocytes have the ability to detoxify chlorinated hydrocarbons.

This investigation demonstrated that ethylene sulfide was consumed in the presence of neutrophils in culture. Ethylene sulfide has not been reported in the exhaled human breath. This observation may suggest that human neutrophils may be able to metabolize carbonyl sulfide.

Several hydrocarbons of interest in exhaled breath research, such as ethane, n-pentane, and acetone were not generated nor consumed by the neutrophils and PBMCs. FIG. 10 illustrates that acetone was seen in the samples containing neutrophils, PBMCs, and media. However, the acetone concentrations from cell culture flasks in which the neutrophils and PBMCs were grown were not significantly different from the headspace acetone obtained from the media only (ethane and n-pentane data not shown). These hydrocarbons have been detected in the exhaled human breath and have been proposed as a means of assessing in vivo lipid peroxidation The glass bioreactor 10 described herein is suitable for collecting the headspace gas above sample. The sample may include a culture of cells, bacteria, or even viruses. The cells, bacteria, or viruses are grown in a controlled and known composition of air by purging the bioreactor of ambient air and replacing it with air containing low levels of volatile organic compounds to minimize the metabolic by-products occurrence from absorbed exogenous sources.

A significant advantage of the bioreactor 10 and methodology is the reduction of contaminating sources. The interior of the bioreactor 10 and associated parts are made of materials such as glass and PTFE, that were found not to outgas VOCs. The two stopcocks 14, 16 allow purging of the bioreactor 10. This makes it possible to replace the ambient air of the laboratory with air containing low concentrations of VOCs and the 5% $CO_2$ typically required for cell culture.

The glass bioreactor 10 may be used to determine certain biomarkers or fingerprints associated with a particular physiological state such as a diseased state. For example, the glass bioreactor 10 could be used in many other clinical situations. For example, gas biomarker discovery for both human cancerous and primary cell cultures and the investigation of gas fingerprints from various bacterial and viral cultures. Identifying cell-specific gas biomarkers using the glass bioreactor 10 may improve our understanding of exhaled human breath gases (i.e., whether the gas is of cellular origin). Furthermore, these gases may be used as disease-specific, microorganism-specific biomarkers for detection and monitoring. Further some emitted gases, e.g. acetaldehyde might be useful in identifying the status of innate immune cells like neutrophils.

Moreover, the biological importance of these compounds, beyond their possible role as gaseous biomarkers, is of interest. For example, acetaldehyde, a known lung irritant, can influence blood coagulation and induce histamine release. The fact that these gases might be produced endogenously by neutrophils leads to the speculation that some of the deleterious effects associated, for example, with pneumonia (characterized by aggregation of neutrophils in the lung) may be due, in part, to the production of these gases by the leukocytes themselves. The glass bioreactor 10 may be used in the drug development of various inflammatory and infectious diseases by examining gas-mediated cellular mechanisms. The bioreactor also can be used as groundwork in developing non-invasive diagnostic tool using exhaled breath gases of various inflammatory and infectious diseases.

While embodiments of the present invention have been shown and described, various modifications may be made without departing from the scope of the present invention. The invention, therefore, should not be limited, except to the following claims, and their equivalents.

What is claimed is:

1. A bioreactor system comprising:
a glass reactor vessel comprising a first glass half comprising an interior volume and a first valve communicating with the interior volume of the first glass half, a second glass half comprising an interior volume and a seal interposed between the first glass half and the second glass half;
a sample holder configured to reside in the interior volume;
a pump system coupled to a source of charge gas having a known composition of volatile organic gases;
a conduit connecting the pump system to the glass reactor vessel, the conduit comprising a non-volatile organic gas emitting material, wherein the first valve is interposed between the conduit and the glass reactor vessel; and
a sample container coupled to the conduit, wherein a second valve is interposed between the sample container and the glass reactor vessel.

2. The bioreactor system of claim 1, further comprising a clamp configured to urge the first glass half and the second glass half toward one another.

3. The bioreactor system of claim 2, wherein the first and second valves comprises stopcocks.

4. The bioreactor system of claim 1, further comprising a manifold operatively coupled to at least one of the first and second valves.

5. The bioreactor system of claim 4, wherein the pump system is operatively coupled to the manifold.

6. The bioreactor system of claim 1, wherein the sample holder comprises a glass or polytetrafluoroethylene vial.

7. The bioreactor system of claim 1, wherein the source of charge gas comprises artificial air.

8. The bioreactor system of claim 1, further comprising a gas chromatography system.

\* \* \* \* \*